United States Patent
Katoh et al.

(10) Patent No.: US 7,442,184 B2
(45) Date of Patent: Oct. 28, 2008

(54) MEDICINAL LIQUID INJECTION CATHETER

(75) Inventors: Osamu Katoh, Kyoto (JP); Masashi Momota, Kamakura (JP); Tomihisa Kato, Anjo (JP)

(73) Assignees: Osamu Katoh, Kyoto-Shi (JP); Asahi Intecc Co., Ltd., Nagoya-Shi (JP)

( * ) Notice: Subject to any disclaimer, the term of this patent is extended or adjusted under 35 U.S.C. 154(b) by 222 days.

(21) Appl. No.: 11/122,733

(22) Filed: May 5, 2005

(65) Prior Publication Data

US 2005/0203462 A1 Sep. 15, 2005

Related U.S. Application Data

(63) Continuation of application No. 10/379,014, filed on Mar. 4, 2003, now Pat. No. 6,926,692.

(30) Foreign Application Priority Data

Mar. 5, 2002 (JP) ............................ 2002-058298

(51) Int. Cl.
 *A61M 29/00* (2006.01)
(52) U.S. Cl. .................................. 604/96.01
(58) Field of Classification Search ............. 604/96.01, 604/101.01, 101.05, 102.01–102.03, 103.04, 604/103.1
See application file for complete search history.

(56) References Cited

U.S. PATENT DOCUMENTS

| | | | |
|---|---|---|---|
| 3,833,003 A | 9/1974 | Taricco | |
| RE31,873 E | 4/1985 | Howes | |
| 4,578,061 A | 3/1986 | Lemelson | |
| 4,601,701 A | 7/1986 | Mueller, Jr. | |
| 4,769,005 A | 9/1988 | Ginsburg et al. | |
| 4,808,156 A | 2/1989 | Dean | |
| 5,059,177 A | 10/1991 | Towne et al. | |
| 5,190,528 A | 3/1993 | Fonger et al. | |
| 5,209,741 A | 5/1993 | Spaeth | |
| 5,261,889 A | 11/1993 | Laine et al. | |
| 5,263,932 A | 11/1993 | Jang | |
| 5,342,301 A | 8/1994 | Saab | |

(Continued)

FOREIGN PATENT DOCUMENTS

EP 0 753 322 A2 1/1997

(Continued)

*Primary Examiner*—Kevin C. Sirmons
*Assistant Examiner*—Elizabeth R MacNeill
(74) *Attorney, Agent, or Firm*—Burr & Brown

(57) ABSTRACT

A medicinal liquid injection catheter includes a flexible main body, a needle-like tubular member, a medicinal liquid supply device, and a balloon. The tubular member is inserted in the main body and an end portion of the tubular member projects from a side hole provided in the main body. The medicinal liquid supply device accommodates a medicinal liquid, and is connected to the tubular member to supply the medicinal liquid through the tubular member. The balloon is attached to an outer portion of the main body and the balloon is expansible in substantially the same direction as a direction in which the portion of the tubular member projects. The medicinal liquid injection catheter additionally includes first and second guide wires. The second guide wire projects from the main body in a direction which intersects a direction in which the first guide wire projects from the main body.

7 Claims, 7 Drawing Sheets

U.S. PATENT DOCUMENTS

| | | | |
|---|---|---|---|
| 5,354,279 | A | 10/1994 | Höfling |
| 5,413,581 | A | 5/1995 | Goy |
| 5,419,777 | A | 5/1995 | Höfling |
| 5,464,395 | A * | 11/1995 | Faxon et al. ............ 604/103.02 |
| 5,569,184 | A | 10/1996 | Crocker et al. |
| 5,797,869 | A | 8/1998 | Martin et al. |
| 5,916,194 | A | 6/1999 | Jacobsen et al. |
| 6,068,610 | A | 5/2000 | Ellis et al. |
| 6,068,638 | A | 5/2000 | Makower |
| 6,135,976 | A * | 10/2000 | Tachibana et al. ............. 604/21 |
| 6,217,554 | B1 | 4/2001 | Green |
| 6,248,122 | B1 * | 6/2001 | Klumb et al. ................ 606/194 |
| 6,283,947 | B1 | 9/2001 | Mirzaee |
| 6,302,870 | B1 * | 10/2001 | Jacobsen et al. ............ 604/272 |
| 6,355,060 | B1 | 3/2002 | Lenker et al. |
| 6,375,615 | B1 * | 4/2002 | Flaherty et al. ............. 600/439 |
| 6,436,090 | B1 | 8/2002 | Sanchez et al. |
| 6,458,098 | B1 * | 10/2002 | Kanesaka ............... 604/101.05 |
| 6,461,296 | B1 | 10/2002 | Desai |
| 6,494,905 | B1 | 12/2002 | Zedler et al. |
| 6,524,302 | B2 | 2/2003 | Kelley |
| 6,544,230 | B1 * | 4/2003 | Flaherty et al. ........ 604/164.12 |
| 6,547,767 | B1 | 4/2003 | Moein |
| 6,689,099 | B2 | 2/2004 | Mirzaee |
| 6,692,466 | B1 | 2/2004 | Chow et al. |
| 6,706,017 | B1 | 3/2004 | Dulguerov |
| 6,884,258 | B2 | 4/2005 | Vardi et al. |
| 6,926,692 | B2 | 8/2005 | Katoh et al. |
| 2001/0011180 | A1 | 8/2001 | Fitzmaurice et al. |
| 2001/0025134 | A1 | 9/2001 | Bon et al. |
| 2002/0055733 | A1 | 5/2002 | Wilson |
| 2002/0072706 | A1 | 6/2002 | Hiblar et al. |
| 2002/0077591 | A1 * | 6/2002 | Happ et al. ............... 604/96.01 |
| 2003/0040712 | A1 | 2/2003 | Ray et al. |
| 2003/0171714 | A1 | 9/2003 | Katoh et al. |
| 2004/0176726 | A1 | 9/2004 | Katoh et al. |

FOREIGN PATENT DOCUMENTS

| | | |
|---|---|---|
| EP | 1 070 513 | 1/2001 |
| EP | 1 342 486 | 9/2003 |
| JP | 05-300946 A1 | 11/1993 |
| JP | 06-32655 | 5/1994 |
| JP | 2001-104487 A1 | 4/2001 |
| JP | 2001-299927 | 10/2001 |
| JP | 2001-299927 A1 | 10/2001 |
| JP | 2001-314514 | 11/2001 |
| JP | 2003-250899 | 9/2003 |
| WO | WO 92/10142 | 6/1992 |
| WO | 99/44539 | 9/1999 |
| WO | WO 01/03762 A1 | 1/2001 |
| WO | WO 01/49357 A2 | 7/2001 |

* cited by examiner

MEDICINAL LIQUID INJECTION CATHETER

CROSS-REFERENCE TO RELATED APPLICATIONS

This application is a continuation of U.S. patent application Ser. No. 10/379,014, filed Mar. 4, 2003, and also claims the benefit of Japanese Patent Application No. 2002-058298, filed on Mar. 5, 2002, entitled "Medicinal liquid injection catheter," the entireties of which are incorporated herein by reference.

BACKGROUND OF THE INVENTION

1. Field of the Invention

The present invention generally relates to a medicinal liquid injection catheter that can inject an appropriate medicinal liquid to a lesion.

2. Discussion of Related Art

A catheter has conventionally been used as a medical device that is inserted, for the purpose of medical treatment or examination, in a human being's tubular organs such as blood vessel, digestive tract, urinary duct, trachea, or bile duct, or other body cavities or tissues. In addition, recently, such a catheter that employs a balloon at an end portion thereof where the balloon is inflatable and deflatable, is usefully used for so-called PTCA (percutaneous transluminal coronary angioplasty) known as a safe method for treating, for example, cardiac infarction or stenocardia. As well known, PTCA is carried out in such a manner that the catheter with the balloon is inserted in a stenotic portion of heart's coronary artery, and the balloon is inflated to push and widen the stenotic portion and thereby improve the flow of blood to the cardiac muscle.

More recently, there are various proposals to use a catheter as a medical device for injecting an appropriate medicinal liquid to a lesion of tissues, e.g., a blood vessel or a tissue near a blood vessel. For example, Japanese Patent Document (Laid-Open Publication) No. 2001-299927 proposes a medicinal liquid injection catheter that employs the above-mentioned balloon.

More specifically described, the medicinal liquid injection catheter disclosed by the above-indicated document includes a tubular main body having a side hole in a side surface thereof (the main body is called a shaft in the document) and a needle-like tubular member (the tubular member is called an introduction needle in the document) that is provided by a flexible, elongate thin tube whose end portion provides a needle portion. The tubular member is inserted and placed in the main body and is movable relative to the main body in a lengthwise direction thereof so that the needle portion projects outward from the side hole of the main body. The medicinal liquid injection catheter also includes a balloon externally attached to the main body to be inflatable and deflatable (the balloon is called an expansible portion in the document).

The medicinal liquid injection catheter having the above-described arrangement assures that the main body is inserted in a blood vessel, then the balloon is expanded to contact and press the blood vessel's wall to prevent the movement of the main body in the blood vessel. In this state, the needle portion of the needle-like tubular member is pushed outward from the side hole of the main body so as to needle a treated lesion. Therefore, the medicinal liquid injection catheter can be used to inject, through the needle-like tubular member, the appropriate medicinal liquid to the lesion.

As explained above, recently, the medicinal liquid injection catheter has been used. However, there has been a demand for a medicinal liquid injection catheter that assures that a main body thereof is fixedly held at a desired position in a tubular organ such as a blood vessel and a needle portion thereof accurately needles a lesion to be treated.

SUMMARY OF THE INVENTION

According to a first aspect of the present invention, there is provided a medicinal liquid injection catheter including a main body having flexibility, a needle-like tubular member, a medicinal liquid supply device, and a balloon. The tubular member is inserted in the main body and an end portion of the tubular member projects from a side hole provided in the main body. The medicinal liquid supply device accommodates a medicinal liquid, and is connected to the tubular member so as to supply the medicinal liquid through the tubular member. The balloon is attached to an outer portion of the main body and the balloon is expansible in substantially the same direction as a direction in which the portion of the tubular member projects.

The medicinal liquid injection catheter constructed as described above assures that when the main body is inserted in, for example, a blood vessel and the balloon is expanded, not only the balloon but also a back surface of the main body that is opposite to the side hole contact with an inner wall of the blood vessel. Therefore, the main body and the inner wall of the blood vessel contact with each other, via respective increased surfaces, so that with an increased frictional force, the main body is fixedly held at a desired position. Thus, the tubular member can accurately needle a lesion or the like.

According to a second aspect of the present invention, there is provided a medicinal liquid injection catheter including a main body having flexibility, a needle-like tubular member, a medicinal liquid supply device, a first guide wire, and a second guide wire. The tubular member is inserted in the main body and an end portion of the tubular member projects from a side hole provided in the main body. The medicinal liquid supply device accommodates a medicinal liquid, and is connected to the tubular member. The first guide wire is inserted in the main body and a distal portion of the first guide wire projects from the main body in a lengthwise direction thereof, and the second guide wire is inserted in the main body and a distal portion of the second guide wire projects from the main body in a direction which intersects the lengthwise direction.

The medicinal liquid injection catheter constructed as described above assures that when the first and second guide wires are inserted in, for example, two branched blood vessels, respectively, the respective portions of the two guide wires project from the main body so as to have a generally V-shaped configuration. Therefore, when the tubular member penetrates into the lesion or the like, a reaction force caused by the penetration is distributed to the two guide wires having the generally V-shaped configuration. Thus, the reaction force is advantageously absorbed, and accordingly the tubular member can be accurately operated to needle the lesion or the like.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE INVENTION

Hereinafter, the embodiment of a medicinal liquid injection catheter according to the present invention will be described in detail by reference to the drawings.

Figure 1:
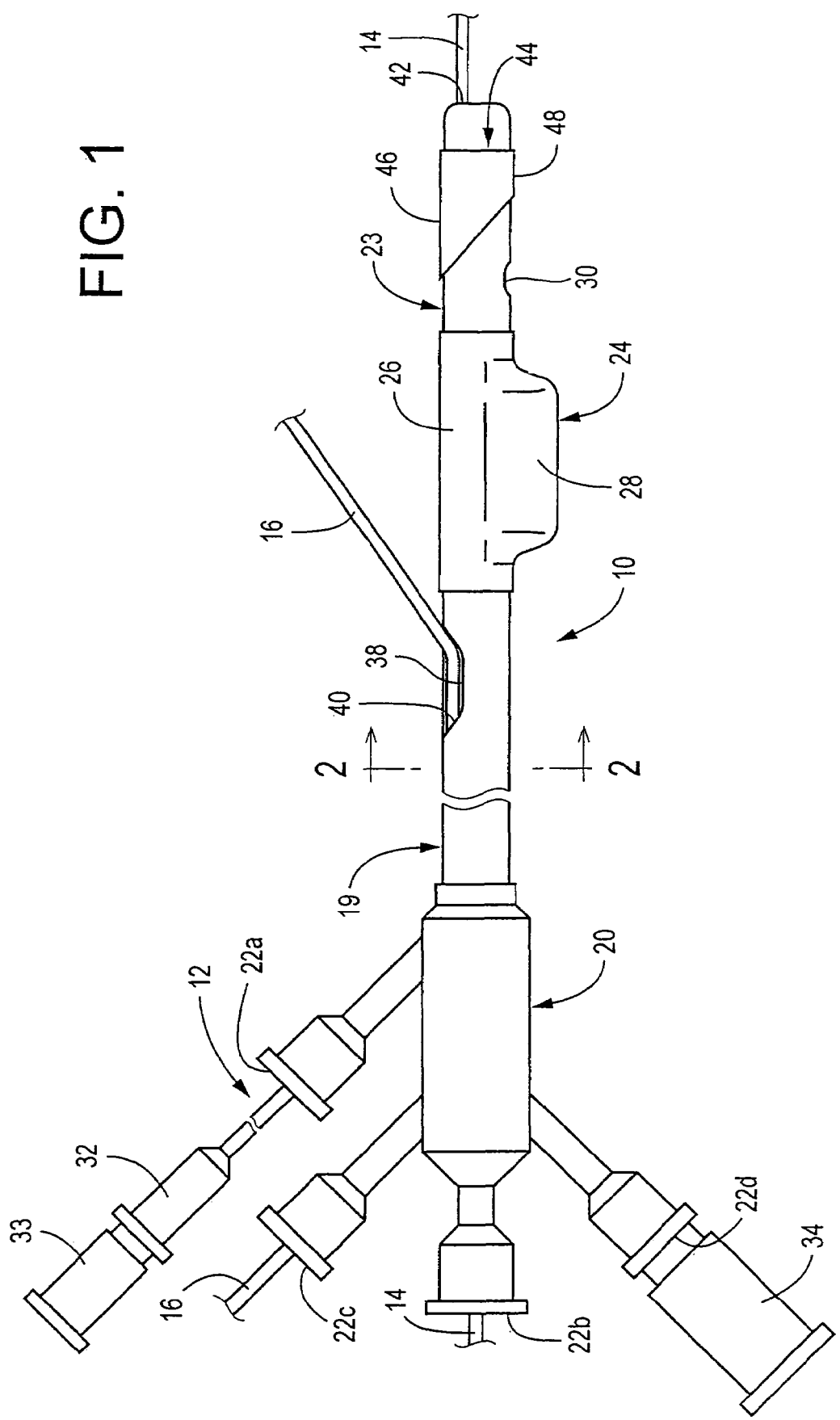
FIG. 1 is an illustrative view schematically showing an embodiment of a medicinal liquid injection catheter according to the present invention.
Figure 2:
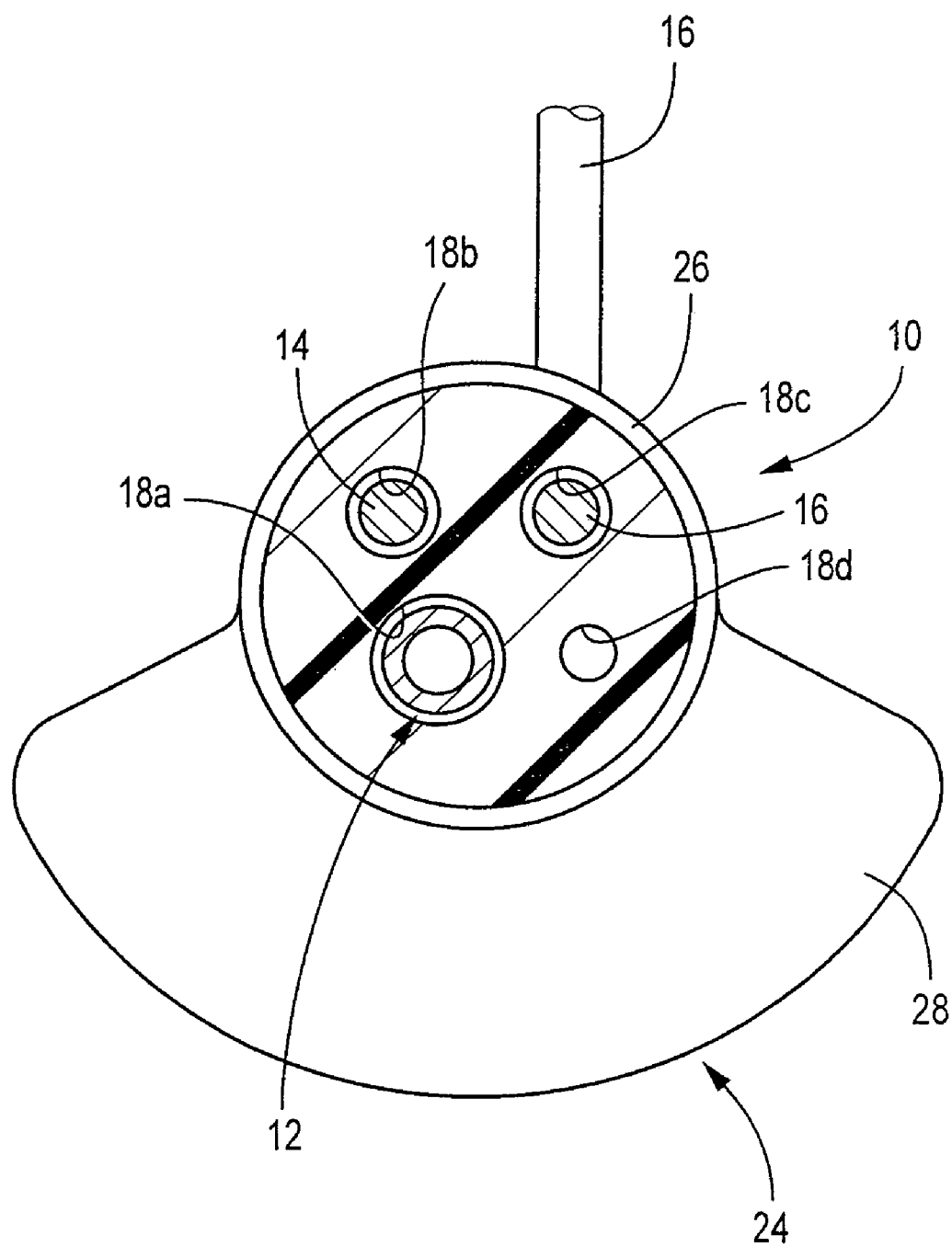
FIG. 2 is an enlarged, cross-sectioned, illustrative view taken along 2-2 in FIG. 1.

FIGS. 1 and 2 respectively show schematic front and transverse-cross-section views of a medicinal liquid injection catheter according to the embodiment. The present medicinal liquid injection catheter is used for injecting a medicinal liquid to a lesion of the cardiac muscle of a patient. In FIGS. 1 and 2, reference numeral 10 designates a main body of the catheter that is provided by an elongate tubular body and accommodates a needle-like tubular member 12, a first guide wire 14, and a second guide wire 16 such that each of those elements 12, 14, and 16 is movable relative to the main body 10 in a lengthwise direction thereof.

More specifically described, the catheter main body 10 has a diameter and a length to be inserted in a blood vessel running from a femoral region or a brachial region of a human body to the heart of the same. The main body 10 has four lumens 18a, 18b, 18c, and 18d that continuously extend therein in the lengthwise direction thereof, and that one independent of each other. In the present embodiment, the catheter main body 10 is formed of a material having a desired elasticity that assures that the main body 10 can be inserted in a tortuous blood vessel; the material may be a synthetic resin material such as polyamide, or a metallic material such as superelastic metal (e.g., Ni—Ti alloy) or stainless steel.

The catheter main body 10 includes a base portion 19 as a rear end portion thereof (i.e., a left-hand end portion thereof as seen in FIG. 1) in a catheter-insertion direction in which the catheter is inserted in a blood vessel, and a connector 20 is attached to the base portion 19. The connector 20 has four inlets 22a, 22b, 22c, and 22d that communicate with the four lumens 18a, 18b, 18c, and 18d, respectively.

The inlet 22a as one of the four inlets 22a-22d communicates with the needle-like-tubular-member lumen 18a having a diameter that is the greatest of respective diameters of the four lumens 18a-18d and is greater than the diameter of the needle-like tubular member 12. The needle-like tubular member 12 is inserted in the needle-like-tubular-member lumen 18a through the inlet 22a. Meanwhile, the two inlets 22b and 22c communicate with the first-guide-wire lumen 18b and the second-guide-wire lumen 18c, respectively, each of which has a diameter that is smaller than the diameter of the needle-like-tubular-member lumen 18a and is greater than respective diameters of the first and second guide wires 14 and 16. The first and second guide wires 14 and 16 are inserted in the first-guide-wire and second-guide-wire lumens 18b and 18c, respectively, through the two inlets 22b and 22c.

In this arrangement, each of the needle-like tubular member 12 and the first and second guide wires 14 and 16 is movable relative to the main body 10 in the lengthwise direction (i.e., axial direction) thereof. The fluid introduction lumen 18d communicates with the inlet 22d as the remaining one of the four inlets 22a-22d. Physiological saline solution, for example, is introduced into the introduction lumen 18d through a syringe (i.e., a fluid supply device) 34 connected to the inlet 22d.

The catheter main body 10 additionally includes a front end portion 23 that is opposite, in the catheter-insertion direction, to the base portion 19 to which the connector 20 is attached. A balloon 24 is attached to the front end portion 23, such that the balloon 24 is inflatable and deflatable.

The balloon 24 is formed of, e.g., a soft synthetic resin material or the same sort of material that is used to form a balloon attached to a balloon catheter used for PTCA. The balloon 24 is integrally formed to include an attachment portion 26 having a tubular shape; and an expansible portion 28 having a bag-like shape that laterally inflates from a substantially half circumferential portion of the attachment portion 26 in a lengthwise intermediate portion thereof. The attachment portion 26 of the balloon 24 fluid-tightly fits on the front end portion 23 of the main body 10, and the expansible portion 28 of the balloon 24 covers a substantially half circumferential portion of the front end portion 23. Although not shown in FIG. 1 or FIG. 2, an inner space of the expansible portion 28 of the balloon 24 communicates with the fluid introduction lumen 18d provided in the catheter main body 10.

Thus, the physiological saline solution introduced through the inlet 22d of the catheter main body 10, is supplied to the expansible portion 28 of the balloon 24 via the fluid introduction lumen 18d. Consequently the expansible portion 28 is expanded in only lateral direction of the main body 10 (i.e., a downward direction as seen in FIGS. 1 and 2). Meanwhile, when the physiological saline solution is discharged from the expansible portion 28 via the introduction lumen 18d and the inlet 22d, the expansible portion 28 is deflated.

Figure 3:
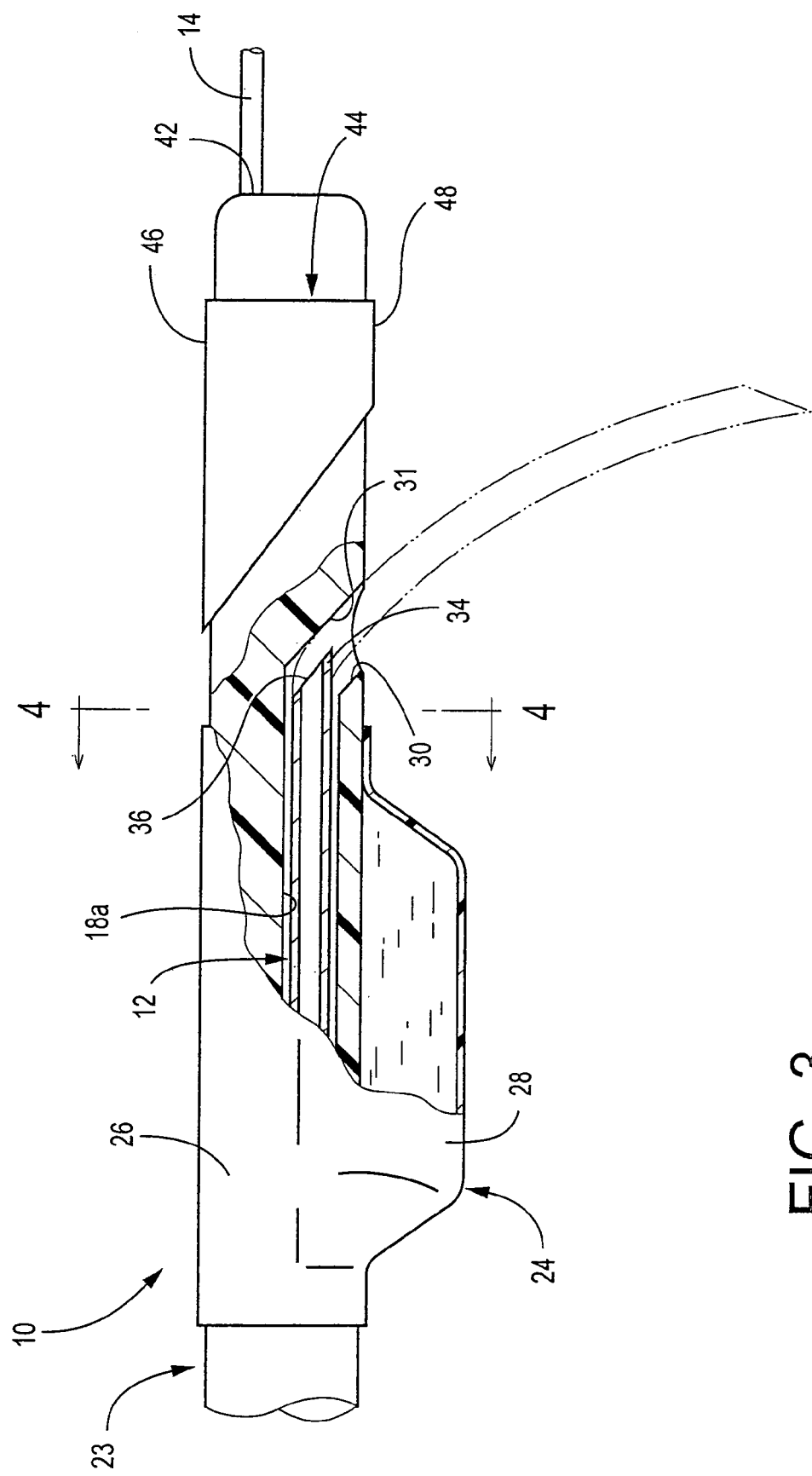
FIG. 3 is an enlarged, partly cut-away, illustrative view showing an important portion of the medicinal liquid injection catheter shown in FIG. 1.

As is seen in FIG. 3, the front end portion 23 of the catheter main body 10, to which the balloon 24 is attached, has a side hole 30 that is located in front side of where the balloon 24 is attached in the catheter-insertion direction. The side hole 30 is formed in a radial direction of the main body 10, and opens toward outside in the same direction as a balloon-expansion direction in which the balloon 24 is expanded (i.e., in the downward direction in FIG. 1). The side hole 30 communicates with the needle-like-tubular-member lumen 18a in which the needle-like tubular member 12 is inserted.

Thus, the needle-like-tubular-member lumen 18a opens, through the side hole 30 formed in the front end portion 23 of the catheter main body 10, in a lateral direction corresponding to the balloon-expansion direction. Thus, the needle-like tubular member 12 is inserted in the lumen 18a such that the tubular member 12 is movable relative to the lumen 18a in the lengthwise direction of the main body 10, i.e., in a direction in which the lumen 18 extends, more specifically described, such that when the tubular member 12 is moved relative to the lumen 18a, a free end portion of the tubular member 12 projects from the side hole 30 in the balloon-expansion direction and retracts into the lumen 18a via the side hole 30. In the present embodiment, an inner part-circumferential surface of the side hole 30 forms an inclined surface 31 that is inclined from the catheter-insertion direction to the direction in which the side hole 30 opens. Thus, the free end portion of the needle-like tubular member 12 can project and retract through the side hole 30 along the inclined surface 31.

The needle-like tubular member 12 is provided by an elongate thin tube that is formed of, for example, a metallic material such as superelastic metal (e.g., Ni—Ti alloy) and the needle-like tubular member 12 is longer than the catheter main body 10. As shown in FIG. 1, a connector 32 is attached to a syringe (i.e., a medicinal liquid supply device) 33 connected to an end portion of the needle-like tubular member 12, while a terminal portion (i.e., a tip portion) of the free end portion of the tubular member 12 that projects or retracts through the side hole 30 in the balloon-expansion direction, provides a sharp needle portion 34 as shown in FIG. 3.

Thus, the needle-like tubular member 12 can be smoothly moved in the needle-like-tubular-member lumen 18a of the catheter main body 10 placed in the tortuous blood vessel; and the free end portion of the tubular member 12, including the needled portion 34, can be smoothly advanced and retracted through the side hole 30 along the inclined surface 31. In the state in which the needle-like tubular member 12 is inserted in the catheter main body 10, a medicinal liquid containing such a gene that promotes vascularization in the cardiac muscle as bFGF (basic fibroblast growth factor), VEGF (vascular endothelial growth factor), HGF (hepatocyte growth factor) or the like is introduced from the syringe 33 via the connector 32 into the tubular member 12, and is discharged through the needle portion 34.

Figure 4:
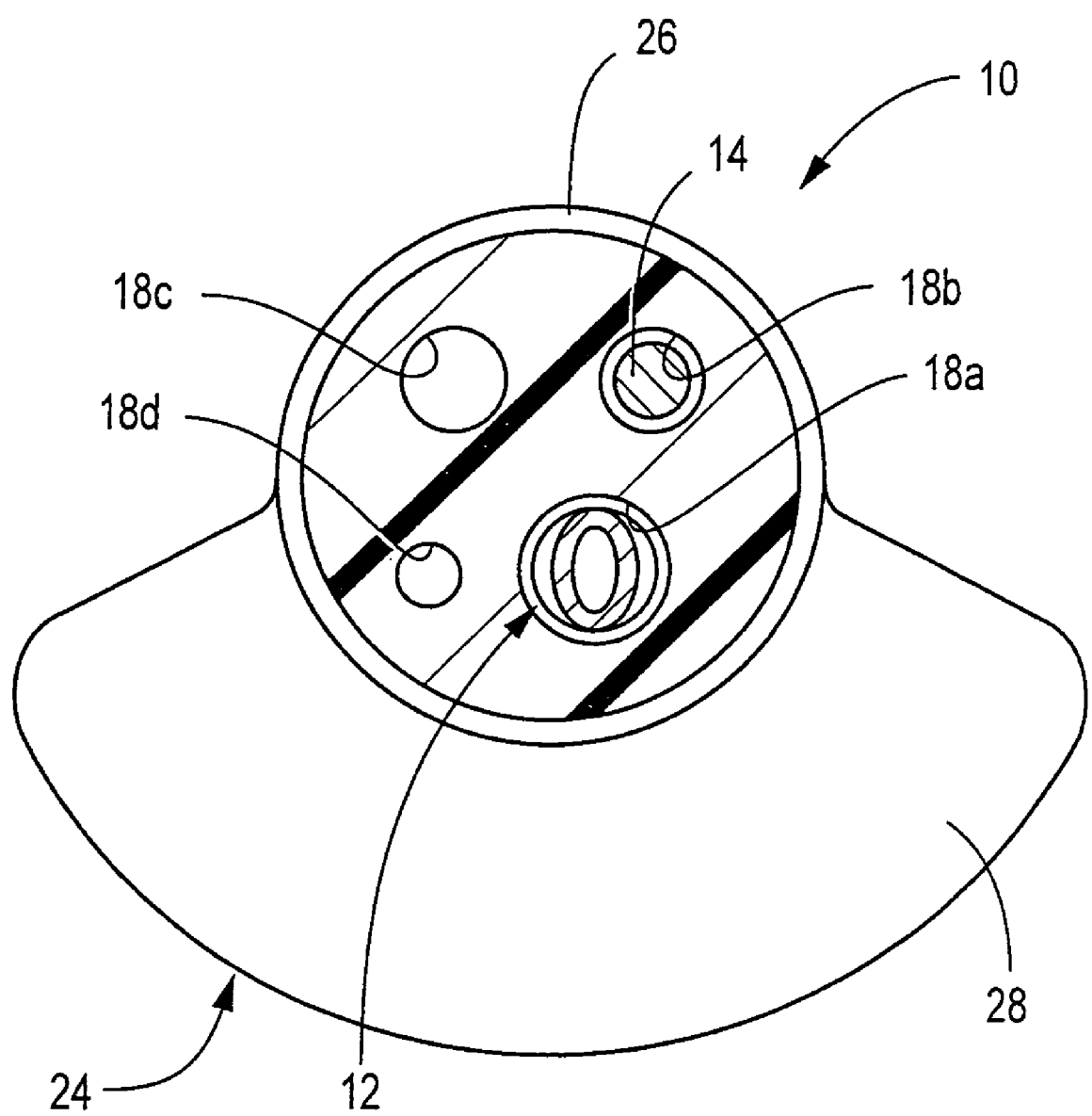
FIG. 4 is an enlarged, cross-sectioned, illustrative view taken along 4-4 in FIG. 3.

As is apparently seen in FIGS. 3 and 4, the needle portion 34 of the needle-like tubular member 12 has an inclined end surface 36 that is inclined in a tubular-member insertion direction in which the tubular member 12 is inserted in the catheter main body 10, i.e., the catheter-insertion direction in which the catheter main body 10 is inserted in the blood vessel. In addition, an end portion of the needle portion 34 has the inclined end surface 36 flattened over a pre-determined length thereof, so that the flattened end portion projected from the side hole 30 exhibits a pre-determined rigidity in the direction of opening of the side hole 30 (i.e., the balloon-expansion direction), and thereby increases geometrical moment of inertia when the needle portion 34 penetrates into the cardiac muscle.

As shown in FIG. 1, the catheter main body 10 has a recess 38 in a portion thereof that is located to the rear of the balloon 24 in the catheter-insertion direction. The recess 38 has two inclined end surfaces facing each other in the lengthwise direction of the main body 10 and are inwardly inclined toward a bottom surface of the recess 38. One of the two inclined end surfaces that is located on the side of the base portion 19 of the main body 10 has a side opening 40 connecting to the second-guide-wire lumen 18c. Thus, the second guide wire 16 inserted in the second-guide-wire lumen 18c projects outward through the side opening 40, and is laterally guided by the other inclined end surface opposed to the side opening 40.

The first-guide-wire lumen 18b in which the first guide wire 14 is inserted extends through the catheter main body 10 in the lengthwise direction thereof and opens outward through an end opening 42 formed in an end surface of the front end portion 23 of the main body 10. Thus, the first guide wire 14 inserted in the first-guide-wire lumen 18b projects outward through the end opening 42 in the catheter-insertion direction.

As shown in FIG. 3, in the present embodiment, a marker tube 44 is fixed to the catheter main body 10 such that the marker tube 44 fits on a portion of the front end portion 23 of the main body 10. The marker tube 44 is located on a front side of the side hole 30 in the catheter-insertion direction. The marker tube 44 is formed of a radiopaque material such as gold, platinum, platinum-rhodium alloy or the like. Since an end of the marker tube 44 is obliquely cut, a tubular wall of the marker tube 44 includes a longest portion 46 and a shortest portion 48 that have the longest axial length and the shortest axial length, respectively, and are diametrically opposite to each other.

The marker tube 44 is fixed to the front end portion 23 of the catheter main body 10, such that the shortest portion 48 thereof is adjacently located on the front side of the side hole 30 in the catheter-insertion direction. Thus, the shortest portion 48 of the marker tube 44 is positioned the side on which the needle portion 34 of the needle-like tubular member 12 projects outward from the side hole 30. The longest portion 46 is thus positioned on a side opposite to the side on which the needle portion 34 projects outward. As a result, in the present embodiment, a rear end of the longest portion 46 indicates a diametrically opposite portion on which the side hole 30 is formed.

Contrarily, if desired, it is possible to fix the marker tube 44 to the catheter main body 10 such that the longest portion 46 is located on the side on which the side hole 30 is formed, and the shortest portion 48 is located on the side opposite to the side on which the side hole 30 is formed.

Since the present catheter has the above-described construction, the marker tube 44 is displayed on a monitor or the like, when an operator inserts the catheter main body 10 into a blood vessel while observing the main body 10 by radioscopy, as will be described later. The operator can determine the axially longest portion, and the axially shortest portion of the marker tube 44 on the monitor to check a ratio between respective lengths of the longest and shortest portions. Since the operator can compare the thus checked ratio with a pre-determined ratio between the lengths of the longest portion 46 and the shortest portion 48 of the marker tube 44, the operator can rotate the main body 10 about its axis until two ratios become substantially equal to each other. Thus, the direction and position of the side hole 30, that is, the position and direction in which the needle portion 34 of the needle-like tubular member 12 projects, can be appropriately placed in a target position.

Figure 5:
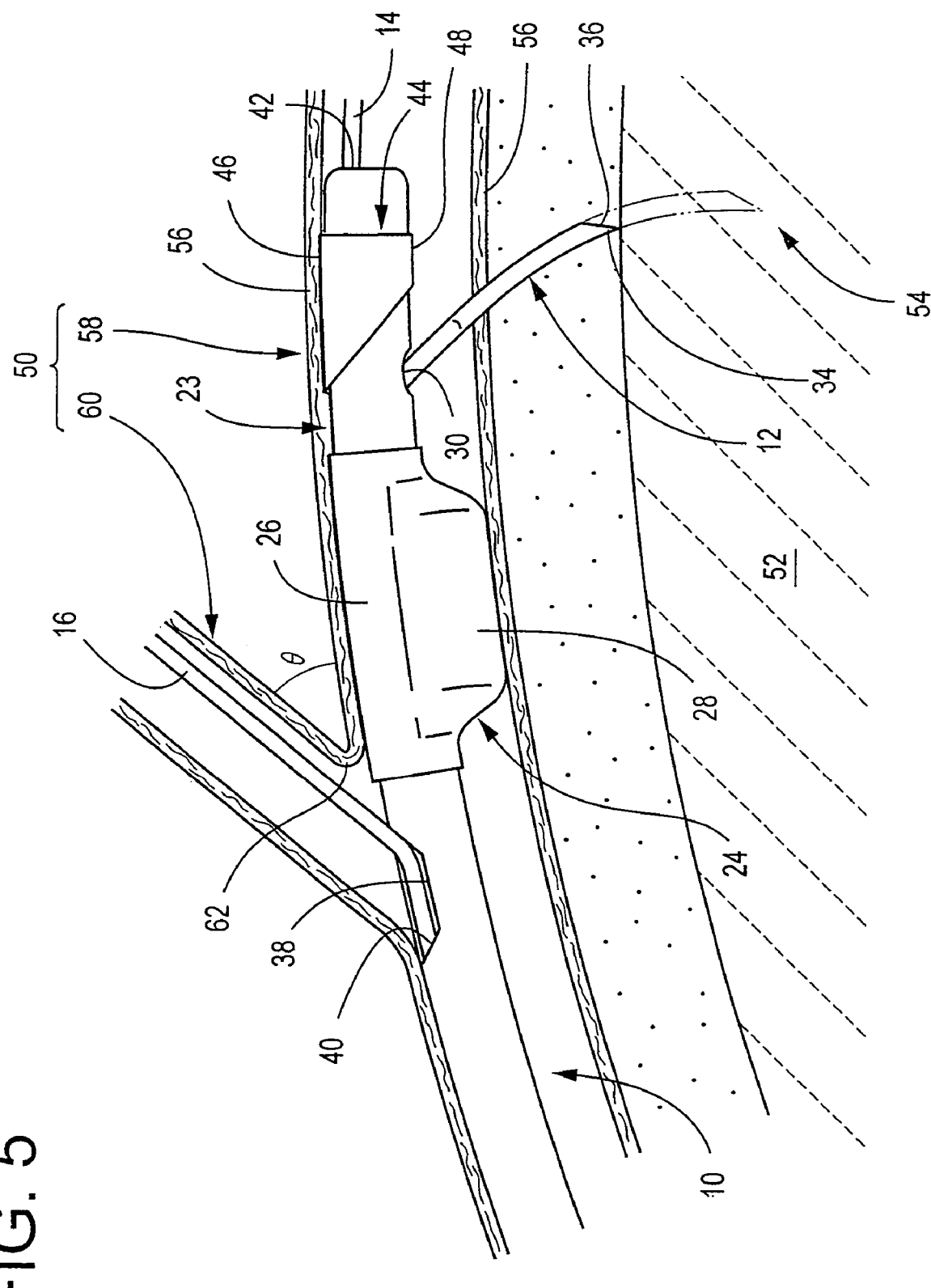
FIG. 5 is an illustrative view showing a state in which the medicinal liquid injection catheter shown in FIG. 1 is used, more particularly, a state in which a main body of the catheter is inserted and positioned in a blood vessel and a needle portion of a needle-like tubular member is operated to needle a lesion.

When the medicinal liquid injection catheter constructed as described above is used for injecting a pre-selected medicinal liquid to a lesion such as a necrotic portion of the cardiac muscle, the catheter main body 10 is inserted into a coronary artery 50 while being guided by the first guide wire 14 inserted from a femoral artery to the coronary artery 50, as shown in FIG. 5, in the same manner as the manner that PTCA is carried out.

The catheter main body 10 is inserted in the coronary artery 50 while the operator observes the position of the marker tube 44 of the main body 10 radioscpically monitored. More specifically described, when the main body 10 is inserted in the coronary artery 50 and the marker tube 44 reaches a target position in the artery 50, the insertion of the main body 10 is temporarily stopped, and then the main body 10 is rotated about its axis while the operator observes the respective positions of the shortest and longest portions 48 and 46 of the marker tube 44, in the previously-described manner. Thus, the shortest portion 48 of the marker tube 44 is so positioned as to face a lesion 54 of cardiac muscle 52 that is located outside the artery 50 via a wall 56 of the coronary artery 50, and accordingly the side hole 30 of the main body 10 is so positioned as to open toward the lesion 54 of the cardiac muscle 52. In addition, the operator recognizes the position of the side hole 30 in the lengthwise direction of the main body 10, while observing the position of the longest portion 46 of the marker tube 44.

In a particular case where the catheter main body 10 is inserted in one branch artery 58 of two branch arteries 58 and 60 of the coronary artery 50, first, the first guide wire 14 is inserted in the one branch artery 58; then the second guide wire 16 is inserted in the other branch artery 60 in which the main body 10 is not inserted. Thus, a branching angle Θ defined by the two branch arteries 58 and 60 is fixed. Subsequently, the main body 10 is inserted into the one branch artery 58. In this way, the main body 10 can be selectively and smoothly inserted in the desired branch artery 58 of the two branch arteries 58 and 60 of the coronary artery 50.

In the above-described case where the first and second guide wires 14 and 16 are inserted in the two branch arteries 58 and 60, respectively, the two guide wires 14 and 16 are extended from the catheter main body 10 so as to take a generally V-shaped configuration. Therefore, as described later, when the needle portion 34 is operated to needle the lesion 54 of the cardiac muscle 52 after the two guide wires 14, 16 and the main body 10 are inserted in the two branch arteries 58 and 60, a reaction force or load produced by the needling is distributed to the two guide wires 14 and 16 extended from the main body 10 to form the V-shaped configuration. Accordingly the position of the needle portion 34 needling the lesion 54 is effectively stabilized.

After the catheter main body 10 is inserted in the coronary artery 50 and is positioned at the desired position in the artery 50, physiological saline solution is introduced into the fluid introduction lumen 18d via the inlet 22d of the connector 20 provided in the base portion 19 of the main body 10, so that the balloon 24 is expanded in the direction in which the side hole 30 opens. Thus, an expanding pressure of the balloon 24 is applied to two portions of the wall 56 of the coronary artery 50 that are one portion contacting with the expansible portion 28 of the balloon 24 and the other portion contacting with the back portion of the attachment portion 26 of the balloon 24 that is opposite to the expansible portion 28. Since the main body 10 is supported by the two portions of the arterial wall 56, the main body 10 is fixedly held in position in the artery 50. In this state, the back portion of the front end portion 23 of the main body 10 that is opposite to the side hole 30 is also held in contact with the arterial wall 56.

Subsequently, the needle-like tubular member 12 inserted in the catheter main body 10 is moved relative to the main body 10, frontward in the catheter-insertion direction, so that the free end portion thereof projects outward in the balloon-expansion direction via the side hole 30. Thus, as indicated at solid line in FIG. 5, the needle portion 34 of the tubular member 12 penetrates the wall 56 of the coronary artery 50, and needles the lesion 54 of the cardiac muscle 52; and, as indicated at chain double-dashed line, the needle portion 34 is further pushed to reach a deep portion of the lesion 54 of the cardiac muscle 52.

Since the back portion of the front end portion 23 of the catheter main body 10 opposite to the side hole 30 is held in contact with the wall 56 of the coronary artery 50, as described above, the reaction force produced by the needling of the needle portion 34 into the cardiac muscle 52 is applied to a portion of the arterial wall 56 that contacts the back portion of the end portion 23 of the main body 10 opposite to the side hole 30. Thus, the reaction force caused by the needling of the needle portion 34 into the cardiac muscle 52 is diffused to the wide portion of the wall 56 of the artery 50 different from the portion of the wall 56 to which the expanding pressure of the balloon 24 is applied.

In the present embodiment of the medicinal liquid injection catheter, the free end surface of the needle portion 34 defines the inclined end surface 36 that is inclined in the direction in which the catheter main body 10 is inserted in the coronary artery 50. When the needle portion 34 is operated to needle the cardiac muscle 52, the inclined end surface 36 contacts the cardiac muscle 52 in the front side thereof in the catheter-insertion direction. Therefore, as the needle portion 34 penetrates into the cardiac muscle 52, a resistance force acts on the inclined end surface 36 of the needle portion 34 in a direction opposite to the catheter-insertion direction. Thus, the needle portion 34 effectively penetrates into even the deep lesion 54 of the cardiac muscle 52, while describing an arcuate locus inwardly curved in the direction opposite to the catheter-insertion direction.

In addition, the free end portion of the needle-like tubular member 12 has the shape flattened in the balloon-expansion direction in the cardiac muscle 52 and accordingly exhibits the increased rigidity or geometrical moment of inertia in that direction. Therefore, the needle portion 34 can well stand the resistance force exerted thereto when the needle portion 34 penetrates into the cardiac muscle 52. Thus, when the needle portion 34 penetrates into the cardiac muscle 52, the needle portion 34 or the free end portion including the needle portion 34 is effectively prevented from being deformed.

When the needle portion 34 penetrates into the cardiac muscle 52 and reaches the target portion of the lesion 54, the operator stops moving the needle-like tubular member 12 relative to the catheter main body 10. Subsequently, the operator introduces the medicinal liquid including the previously-described gene that promotes the vascularization in the cardiac muscle 52 from the syringe 33 provided in the base end portion of the tubular member 12, so that the medicinal liquid is discharged from the opening of the needle portion 34 and is injected to the lesion 54 of the cardiac muscle 52.

The medicinal liquid injection catheter having the above-described arrangement assures that the catheter main body 10 can be inserted along the first guide wire 14 placed in the coronary artery 50, and is located at the desired position in the artery 50 where the balloon 24 is to be expanded. In addition to the operation like PTCA, the present catheter assures that the medicinal liquid can be injected to the lesion 54 of the cardiac muscle 52 to be cured, by just carrying out a very simple and easy operation that the needle portion 34 of the needle-like tubular member 12 inserted in the main body 10 is pushed outward to needle the lesion 54 of the cardiac muscle 52 and the medicinal liquid is introduced into the tubular member 12. Thus, the treatment of the lesion 54 of the cardiac muscle 52 can be very effectively done by the simple and easy technique and operation like those of PTCA.

In addition, the medicinal liquid injection catheter assures that two different portions of the wall 56 of the coronary artery 50 respectively receive the expanding pressure of the balloon 24 and the reaction force caused by the needling of the needle portion 34 into the cardiac muscle 52. Thus, the arterial wall 56 is very effectively prevented from being excessively expanded because the expanding pressure of the balloon 24 and the reaction force of the needling of the needle portion 34 do not act on a same portion of the wall 56. That is, the needle portion 34 can accurately needle the lesion 54 of the cardiac muscle 52 to be cured without the excessive expansion of the coronary artery 50. As a result, the medicinal liquid can be accurately and smoothly fed to the lesion 54 of the cardiac muscle 52, without the problem of dissociation of tunica intima or tunica media of the coronary artery 50 that might be caused by the excessive expansion of the arterial wall 56.

In addition, the medicinal liquid injection catheter assures that in the state in which the catheter main body 10 is fixedly held with the expansion of the balloon 24, at the desired position in the coronary artery 50, if the needle portion 34 of the needle-like tubular member 12 is pushed outward to needle the lesion 54 of the cardiac muscle 52, a large-area including the expansible portion 28 of the balloon 24 and the back portion of the attachment portion 26 that is opposite to the side on which the balloon 24 expands, contacts with the wall 56 of the coronary artery 50. Therefore, when the needle portion 34 needles the cardiac muscle 52, the reaction force caused by the needling produces a great frictional force between the front end portion 23 of the main body 10 and the arterial wall 56, so that the main body 10 is fixedly held in the coronary artery 50.

Additionally, the medicinal liquid injection catheter assures that the needle portion 34 needles into the cardiac muscle 52 with the back portion of the front end portion 23, opposite to the side hole 30, contacting with the arterial wall 56. Therefore, the front end portion 23 of the main body 10 is advantageously prevented from being bent or deformed by the reaction force caused by the needling of the needle portion 34, and accordingly the direction in which the needle portion 34 is pushed outward from the side hole 30 is stabilized. Thus, the needle portion 34 can be more accurately reached to the target portion of the lesion 54 of the cardiac muscle 52.

Moreover, in the embodiment of the medicinal liquid injection catheter, the needle portion 34 of the needle-like tubular member 12 is projected outward from the side hole 30 located in front of the balloon 24 in the catheter-insertion direction, so that the needle portion 34 needles the lesion 54 of the cardiac muscle 52. Therefore, even in a particular case where the needle portion 34 needles a small-diameter portion of the coronary artery 50 or an inelastic artery because of serious condition, the balloon 24 can be normally expanded in a safer portion of the artery 50 that is located proximal side of the above-indicated portion, so that the needle portion 34 can needle the distal target portion of the lesion 54 of the cardiac muscle 52.

In addition, in the medicinal liquid injection catheter, the end surface of the needle portion 34 of the needle-like tubular member 12 defines the inclined end surface 36 that is inclined in the previously-described direction. Therefore, the needle portion 34 can deeply penetrate the lesion 54 of the cardiac muscle 52 while describing the arcuate locus extending in the rearward direction opposite to the catheter-insertion direction. Thus, the needle portion 34 can effectively reach the target portion of the lesion 54 of the cardiac muscle 52. This means that the overall length of the needle-like tubular member 12 can be advantageously shortened.

Furthermore, in the medicinal liquid injection catheter, the marker tube 44 formed of the radiopaque material is attached to the front end portion 23 of the catheter main body 10. Therefore, the operator can insert the main body 10 into the coronary artery 50 while observing the position of the marker tube 44 by radioscopy, and thereby accurately position the front end portion 23 at the desired position in the coronary artery 50. In addition, the operator can adjust the respective positions of the longest and shortest portions 46 and 48 of the marker tube 44, and thereby place the side hole 30 of the main body 10 in the desired position in the artery 50 so that the side hole 30 opens toward the lesion 54 of the cardiac muscle 52. Thus, the operator can accurately recognize the position and direction in which the needle portion 34 is pushed outward, and accordingly the needle portion 34 can be quickly and accurately operated to needle the lesion 54 of the cardiac muscle 52.

While the present invention has been described in its preferred embodiment, it is to be understood that the present invention is by no means limited to the details of the illustrated embodiment but may be otherwise embodied.

For example, in the embodiment of the medicinal liquid injection catheter, only one balloon 24 is attached to the front end portion 23 of the catheter main body 10, such that the single balloon 24 is expansible in the same direction as the direction in which the side hole 30 opens. However, in addition to the balloon 24, it is possible to attach an auxiliary balloon to the front end portion 23 of the main body 10.

Figure 6:
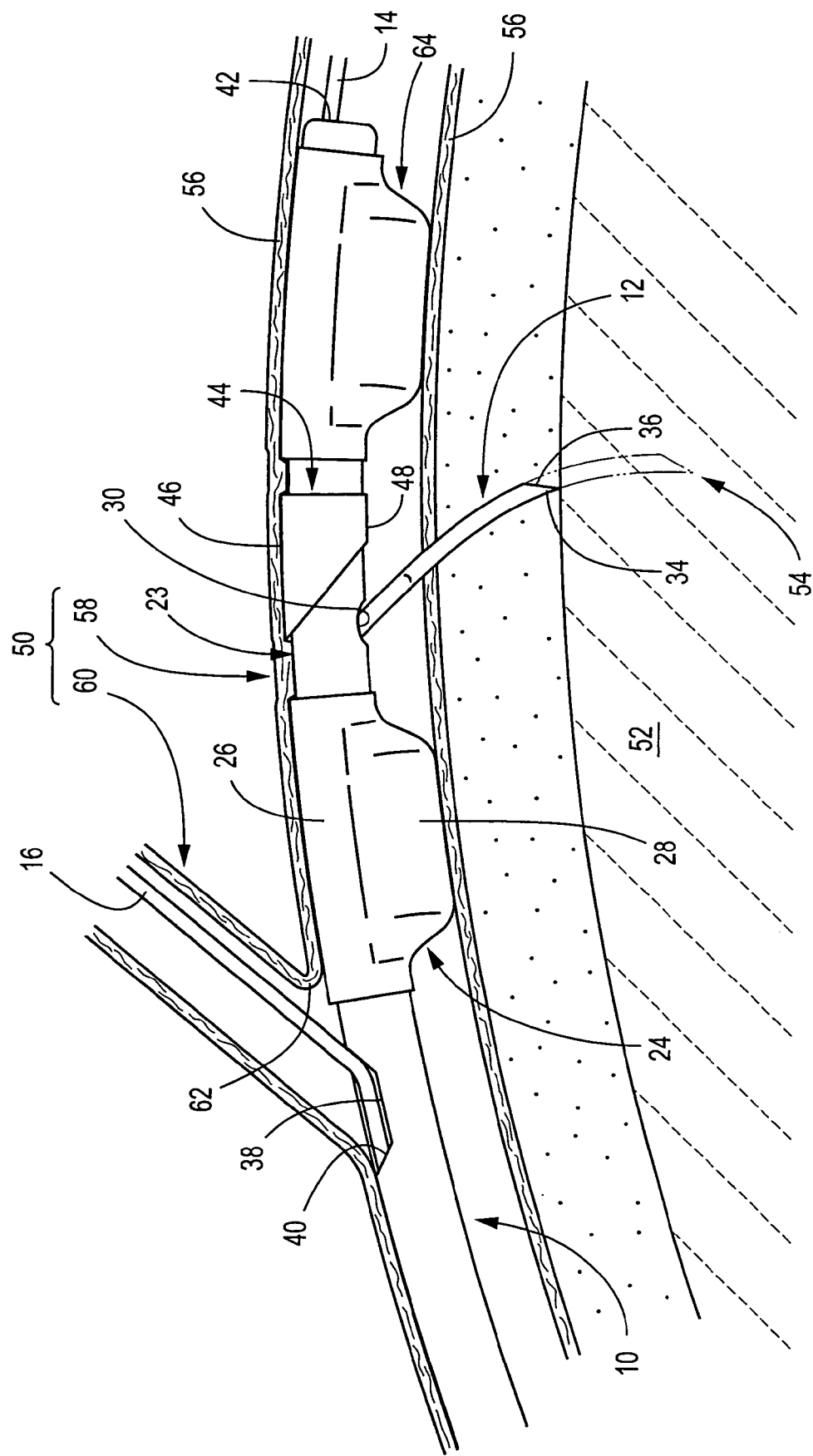
FIG. 6 is a view corresponding to FIG. 5, showing another embodiment of the medicinal liquid injection catheter according to the present invention.

Namely, in another embodiment of the present embodiment shown in FIG. 6, it is possible to attach, not only the balloon 24 to the rear portion of the side hole 30 in the catheter-insertion direction, such that the balloon 24 is expansible in only one lateral direction, but also an auxiliary balloon 64 to a front portion of the side hole 30 in the catheter-insertion direction, such that the auxiliary balloon 64 is expansible in only the same lateral direction as the direction in which the balloon 24 is expansible.

Since the two balloons 24 and 64 expand, the sum of respective expanding pressures of the two balloons 24 and 64 acts on the arterial wall 56, so an increased frictional force is produced between the front end portion 23 and the arterial wall 56. Therefore, the force holding the main body 10 in the coronary artery 50 can be more effectively increased. As a result, the positioning accuracy and the needling force of the needle portion 34 of the needle-like tubular member 12 can be more effectively increased.

Generally, during a surgical operation, a coronary spasm that the artery is suddenly constricted may occur because of, for example, illness of tunica intima of the coronary artery 50, it may prevent the operator from removing the catheter main body 10 from the artery 50. In this case, however, after the needle portion 34 is retracted into the main body 10, either one, or both, of the two balloons 24 and 64 can be so deflated as to release the blood retained between the two balloons 24 and 64 and thereby assure that blood normally flows through the artery 50. In this state, the main body 10 can be easily drawn out of the coronary artery 50.

Figure 7:
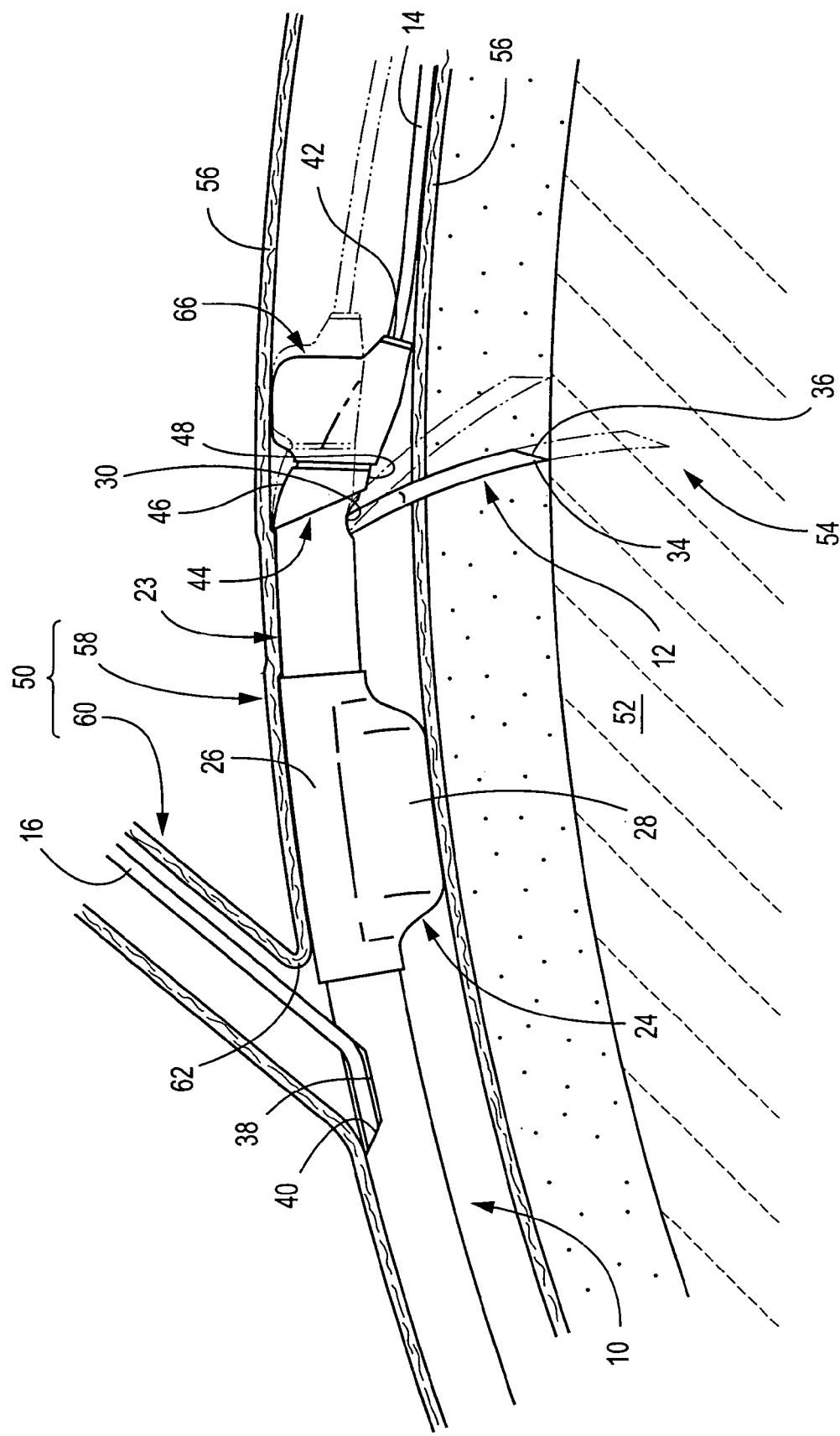
FIG. 7 is a view corresponding to FIG. 5, showing yet another embodiment of the medicinal liquid injection catheter according to the present invention.

Moreover, in yet another embodiment of the present embodiment shown in FIG. 7, it is possible to attach an auxiliary balloon 66 to a front-side portion of the front end portion 23 of the catheter main body 10 that is located in front of the side hole 30 in the catheter-insertion direction, such that the auxiliary balloon 66 is expansible in only one lateral direction opposite to the lateral direction in which the balloon 24 expands.

In the above embodiment, for example, in a state in which the balloon 24 is expanded and the catheter main body 10 is held at a desired position in the coronary artery 50, the auxiliary balloon 66 can be expanded as indicated at solid line or chain double-dashed line in FIG. 7. As a result, the front-side portion of the front end portion 23 to which the auxiliary balloon 66 is attached is bent in a direction opposite to the direction in which the auxiliary balloon 66 is expanded, and accordingly the direction in which the side hole 30 formed in the front end portion 23 opens is changed.

The medicinal liquid injection catheter having the above-described auxiliary balloon 66 assures that the amount of expansion of the auxiliary balloon 66 can be changed as needed and accordingly the direction in which the needle portion 34 is pushed outward through the side hole 30 can be appropriately adjusted. Thus, the position where the needle portion 34 needles the lesion 54 of the cardiac muscle 52 can be easily changed without displacing the catheter main body 10 held in the coronary artery 50.

In the above embodiment of the medicinal liquid injection catheter, the marker tube 44 is attached to only the front end portion 23 of the catheter main body 10. However, it is possible to attach an auxiliary marker tube, having a structure similar to that of the marker tube 44, to the free end portion of the needle-like tubular member 12. In this modification, the auxiliary marker tube has an inclined end surface that defines a longest portion and a shortest portion, and is attached to a position near the needle portion 34, such that a direction of inclination of the inclined end surface of the auxiliary marker tube is parallel, or opposite, to the direction of inclination of the inclined end surface 36 of the needle portion 34. Therefore, when the operator operates, under radioscopy, the needle portion 34 to needle the lesion 54 of the cardiac muscle 52, the operator can clearly observe the direction of inclination of the inclined end surface 36 of the needle portion 34, and thereby can more accurately operate the needle portion 34 to appropriately penetrate the lesion 54 while the needle portion 34 describes the arcuate locus directed in the rearward direction opposite to the catheter-insertion direction.

In addition, other arrangements commonly known may be employed, as needed, as an arrangement for moving the needle-like tubular member 12 in the catheter main body 10, and a method for inflating and deflating the balloon 24 and/or the auxiliary balloons 64, 66. Moreover, respective shapes of those arrangements are by no means limited.

Additionally, in the medicinal liquid injection catheter having the above-described arrangement, the second guide wire 16 may not be employed.

The above-described embodiments of the present invention relate to the medicinal liquid injection catheter that is used to inject the medicinal liquid to the lesion of the cardiac muscle and thereby treat the lesion. However, the present invention can be advantageously applied to various sorts of medicinal liquid injection catheters that are used to inject respective appropriate medicinal liquids to various sorts of lesions that occur to other sorts of muscles than the cardiac muscle, blood vessels, or the like.

While the present invention has been described in detail in its preferred embodiments, it is to be understood that the present invention may be embodied with various changes, modifications, and improvements which may occur to a person skilled in the art without departing from the scope and spirit of the present invention.

What is claimed is:

1. A method of injecting a medicinal liquid into a living being comprising:
    inserting a first guide wire into a first living being lumen;
    inserting a second guide wire into a second living being lumen branched from the first living being lumen;
    inserting a distal insertion end of a tubular main body into the first living being lumen along the first and second guide wires such that (i) the first guide wire is inserted in a first guide wire lumen provided in the tubular main body, and the second guide wire is inserted in a second guide wire lumen provided in the tubular main body, (ii) a distal end portion of the second guide wire projects through a side of the tubular main body at a second guide wire projection location, (iii) the second guide wire remains inserted in the second living being lumen, (iv) the first guide wire lumen and the second guide wire lumen are spaced apart from one another and disposed away from an axial center of the tubular main body, and (v) a first imaginary line extends between a center of the first guide wire lumen and a center of the second guide wire lumen when viewed in cross section;
    inserting a tubular member into a tubular member lumen, the center of the tubular member lumen being provided within a region of the tubular main body, when viewed in cross section, that is defined by second and third imaginary lines, the second imaginary line passing through the center of the first guide wire lumen and being perpendicular to the first imaginary line and the third imaginary line passing through the center of the second guide wire lumen and being perpendicular to the first imaginary line;
    projecting an end portion of the tubular member from the tubular main body into the living being through a side wall of the first living being lumen while the first guide wire is extended beyond the distal insertion end of the tubular main body by a substantial distance and the second guide wire is extended beyond the side of the tubular main body by a substantial distance, the tubular member projecting from a tubular member projection location that is located at an axial distance from the distal insertion end of the tubular main body, the axial distance between the distal insertion end of the tubular main body and the tubular member projection location is the same as or less than an axial distance between the distal insertion end of the tubular main body and the second guide wire projection location, wherein the end portion of the tubular member projects in a different direction from each of directions in which the first and second guide wires are respectively extended into the first and second living being lumens; and
    supplying the medicinal liquid into the living being through the tubular member while the first guide wire is extended beyond the distal insertion end of the tubular main body by a substantial distance and the second guide wire is extended beyond the side of the tubular main body by a substantial distance.

2. The method of injecting a medicinal liquid into a living being according to claim 1, further comprising expanding a first balloon attached in the tubular main body before the end portion of the tubular member is projected into the living being.

3. The method of injecting a medicinal liquid into a living being according to claim 2, wherein the first balloon expands in substantially a same direction as a direction in which the end portion of the tubular member projects.

4. The method of injecting a medicinal liquid into a living being according to claim 2, wherein the tubular member projects from the tubular main body at a projection location along a lengthwise direction of the tubular main body, the projection location being separated from the first balloon such that an entirety of the first balloon is located a distance further from the distal insertion end of the tubular main body than the projection location.

5. The method of injecting a medicinal liquid into a living being according to claim 3, further comprising expanding a second balloon attached in the tubular main body in a front portion where the tubular member projects in a direction in which the tubular main body is inserted before the end portion of the tubular member is projected into the living being, wherein the second balloon expands in substantially a same direction as a direction in which the first balloon is expansible.

6. The method of injecting a medicinal liquid into a living being according to claim 3, further comprising expanding a second balloon attached in the tubular main body in a front portion where the tubular member projects in a direction in which the tubular main body is inserted before the end portion of the tubular member is projected into the living being, wherein the second balloon expands in substantially an opposite direction to a direction in which the first balloon is expansible.

7. The method of injecting a medicinal liquid into a living being according to claim 1, further comprising adjusting a position of a circumferential direction of the tubular main body to project the end portion of the tubular member with a radiopaque marker provided in vicinity of the portion where the tubular member projects before the end portion of the tubular member is projected into the living being.

* * * * *